United States Patent [19]

Vecchietti et al.

[11] Patent Number: 5,428,042

[45] Date of Patent: Jun. 27, 1995

[54] 1-(2H-1-OXO-3,4-DIHYDRONAPHTYL-6-YL)-ACETYL-PIPERIDINES AS KAPPA AGONISTS

[75] Inventors: Vittorio Vecchietti; Roberto Colle; Giuseppe Giardina, all of Milan, Italy

[73] Assignee: Dr Lo Zambeletti S.p.A., Milan, Italy

[21] Appl. No.: 940,858

[22] PCT Filed: Apr. 12, 1991

[86] PCT No.: PCT/EP91/00717

§ 371 Date: Dec. 23, 1992

§ 102(e) Date: Dec. 23, 1992

[87] PCT Pub. No.: WO91/17116

PCT Pub. Date: Nov. 14, 1991

[30] Foreign Application Priority Data

Apr. 28, 1990 [GB] United Kingdom ......... 9009604
Dec. 13, 1990 [GB] United Kingdom ......... 9027100

[51] Int. Cl.$^6$ ............. A61K 31/445; C07D 211/16; C07D 211/26
[52] U.S. Cl. .................... 514/319; 546/206
[58] Field of Search ............ 546/206; 514/319

[56] References Cited

U.S. PATENT DOCUMENTS

| | | | |
|---|---|---|---|
| 4,753,952 | 6/1988 | Vecchietti | 514/307 |
| 4,806,547 | 2/1989 | Giardina | 514/307 |
| 4,826,819 | 5/1989 | Vecchietti | 514/212 |
| 4,999,359 | 3/1991 | Vecchietti | 514/301 |
| 5,030,649 | 7/1991 | Vecchietti | 514/428 |
| 5,041,451 | 8/1991 | Colle | 514/301 |
| 5,087,630 | 2/1992 | Colle | 514/307 |
| 5,089,507 | 2/1992 | Vecchietti | 514/326 |
| 5,254,564 | 10/1993 | Vecchietti | 514/307 |

FOREIGN PATENT DOCUMENTS

| | | |
|---|---|---|
| 0232612 | 8/1987 | European Pat. Off. |
| 0333315 | 9/1987 | European Pat. Off. |
| 0275696 | 7/1988 | European Pat. Off. |
| 0330461 | 8/1989 | European Pat. Off. |
| 0330467 | 8/1989 | European Pat. Off. |
| 0330469 | 8/1989 | European Pat. Off. |
| 0356247 | 2/1990 | European Pat. Off. |
| 0366327 | 5/1990 | European Pat. Off. |
| 0374756 | 6/1990 | European Pat. Off. |
| 3409237 | 9/1985 | Germany |
| 3523002 | 1/1987 | Germany |
| 3643667 | 6/1988 | Germany |
| WO91/08205 | 6/1991 | WIPO |
| WO91/08206 | 6/1991 | WIPO |
| WO91/17116 | 11/1991 | WIPO |
| WO92/15304 | 9/1992 | WIPO |
| WO92/15592 | 9/1993 | WIPO |

OTHER PUBLICATIONS

Engel et al., J. Med. Chem., 32(8), 1718–1724 1989.
Brooks et al., *Opiate Receptors within the Blood–Brain Barrier Mediate Kappa Agonists-Induced Water Diuresis*, J. Pharmacol. Exp. Ther., 266, 164 (1993).
Silvia et al., Protection from ischemia-induced cerebral edema in the rat by U-50488H, a kappa opioid receptor agonist, Brain Res., 403, 52 (1987).
Hall et al., Stroke, Quantitative Analysis of Effects of κ-Opioid Agonists on Postischemic Hippocampal CA1 Neuronal Necrosis in Gerbils, 19, 8 1008 (1988).
Journal of Medicinal Chemistry, vol. 32, No. 8, Aug. 1989, American Chemical Society, (Washington, D.C., US) W. W. Engel et al: "Tricyclic compounds as selective muscarinic receptor antagonists. 3. Structure–selectivity relationships in a series of cardioselective (M2) anti-muscarinics", pp. 1718–1724.

Primary Examiner—Raymond Henley, III
Assistant Examiner—Phyllis G. Spivack
Attorney, Agent, or Firm—Charles M. Kinzig; Stephen Venetianer; Edward T. Lentz

[57] ABSTRACT

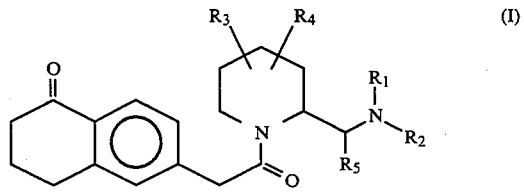

Azacyclic derivatives of formula (I), in which $R_1$ and $R_2$ are each linear or branched alkyl, cycloalkyl, cycloalkylalkyl, alkenyl, cycloalkenyl or alkynyl; $R_3$ and $R_4$ are identical, and each is a hydrogen or alkyl; and $R_5$ is hydrogen or alkyl, and their use in medicine are disclosed.

8 Claims, No Drawings

1-(2H-1-OXO-3,4-DIHYDRONAPHTYL-6-YL)-ACETYL-PIPERIDINES AS KAPPA AGONISTS

This invention is concerned with novel azacyclic derivatives, processes for their preparation, and their use in medicine.

Compounds which are kappa-receptor agonists act as analgesics through interaction with kappa opioid receptors. The advantage of kappa-receptor agonists over the classical $\mu$-receptor agonists, such as morphine, lies in their ability to cause analgesia while being devoid of morphine-like behavioural effects and addiction liability.

European Published Application Nos. 333315 and 361791 disclose groups of azacyclic derivatives which exhibit kappa-receptor agonism without some of the behavioural effects of morphine and morphine analogues, and which are thus of potential therapeutic utility as analgesics.

Certain azacyclic derivatives falling within the scopes of the above European Applications, but not specifically disclosed therein, have now been discovered which also exhibit potent kappa-receptor agonism and are potentially useful as analgesics, including peripheral analgesics for treating inflammatory pain.

These derivatives show a diminished affinity for kappa brain receptors while retaining effective analgesic activity. The derivatives are also of potential use in the treatment of cerebral ischaemia.

According to the present invention there is provided a compound, or a solvate or salt thereof, of (I):

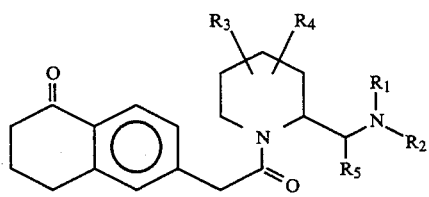

in which:
$R_1$ and $R_2$ are each linear or branched $C_{3-4}$ alkyl, $C_{3-6}$ cycloalkyl, $C_{4-6}$ cycloalkylalkyl, $C_{3-4}$ alkenyl, $C_{3-6}$ cycloalkenyl or $C_{3-4}$ alkynyl,
$R_3$ and $R_4$ are identical, and each is hydrogen or $C_{1-4}$ alkyl; and
$R_5$ is hydrogen or $C_{1-3}$ alkyl.

Preferably, when $R_3$ and $R_4$ are $C_{1-4}$ alkyl they are both bonded to the same carbon atom of the piperidine ring, thereby forming a gem-dialkyl grouping.

When $R_5$ is $C_{1-3}$ alkyl, $R_3$ and $R_4$ are preferably hydrogen.

Examples of $R_1$ and $R_2$ are methyl, ethyl, propyl, isopropyl, tert-butyl, cyclopropyl, cyclobutyl, cyclopentyl, cyclopropylmethyl, allyl, and propynyl.

Examples of $R_3$ and $R_4$ are hydrogen, 3,3 gem-dimethyl, 4,4 gem-dimethyl and 5,5 gem-dimethyl. Examples of $R_5$ are hydrogen and methyl.

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of pharmaceutically acceptable solvates of a compound of formula I include hydrates.

The compounds of formula I have an asymmetric centre and therefore exist in more than one stereoisomeric form. The invention extends to all such forms and to mixtures thereof, including racemates.

The present invention also provides a process for the preparation of a compound of formula I which comprises reacting a compound of formula (II):

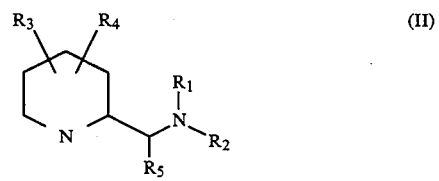

in which $R_1$, $R_2$, $R_3$, $R_4$, and $R_5$ are as defined for formula (I), with a compound of formula (III):

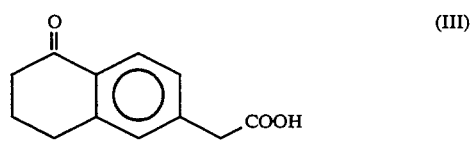

or an active derivative thereof,
and then optionally forming a salt and/or solvate of the obtained compound of formula (I).

Suitable active derivatives of the compound of formula (III) are the acid chloride or acid anhydride. Another suitable derivative is a mixed anhydride formed between the acid and an alkyl chloroformate.

For example, in standard methods well known to those skilled in the art, the compound of formula (II) may be coupled:
a) with an acid chloride in the presence of an inorganic or organic base,
b) with the acid in the presence of dicyclohexyl carbodiimide, N-dimethylaminopropyl-N'-ethyl carbodiimide or carbonyl diimidazole,
c) with a mixed anhydride generated in situ from the acid and an alkyl (for example ethyl)chloroformate.

The compounds of formula I may be converted into their pharmaceutically acceptable acid addition salts by reaction with the appropriate organic or mineral acids. Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

As mentioned before, the compounds of formula I exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form.

Compounds of formula (II) may be prepared according to the following reaction Scheme I:

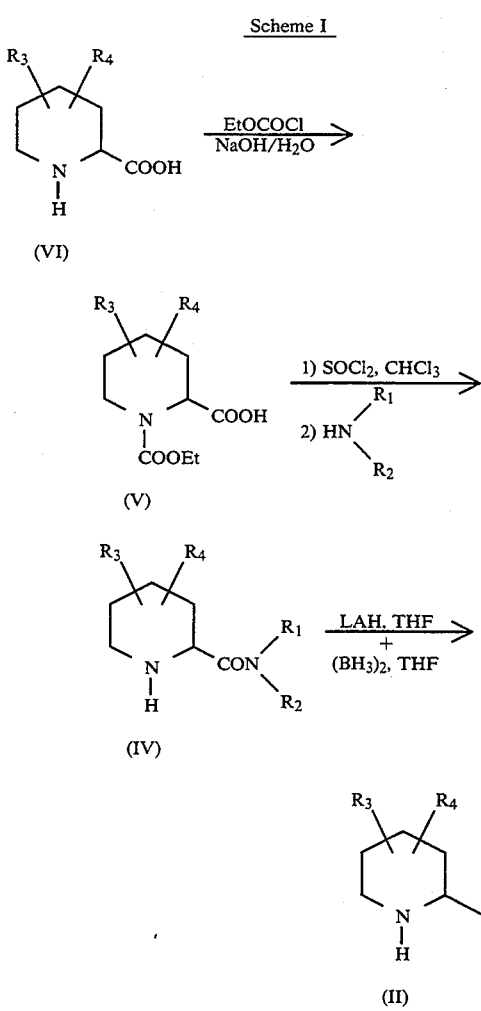

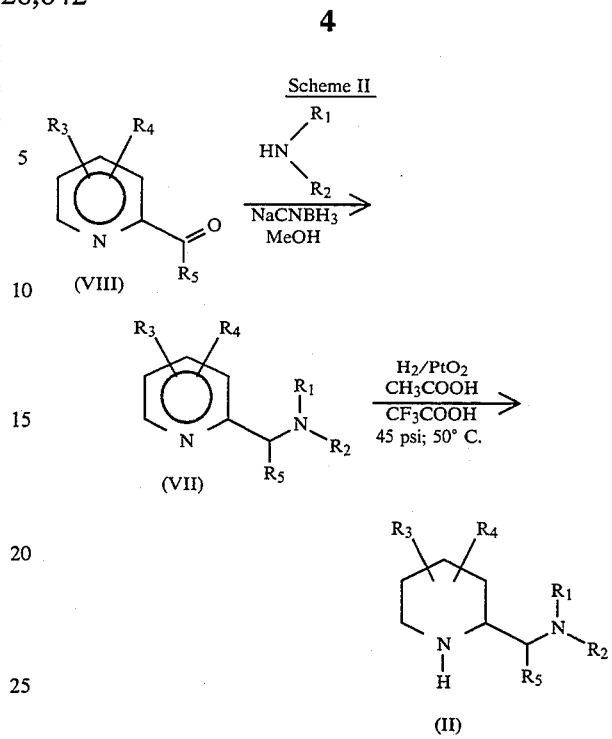

In this scheme, an acid of formula (VI) is firstly nitrogen-protected with an ethoxycarbonyl protecting group to form a compound of formula (V) which is then reacted with an amine $NHR_1R_2$ (in which $R_1$ and $R_2$ are as defined earlier) to obtain an N-deprotected amide of formula (IV). This amide is then reduced to a diamine of formula (II) by conventional means.

Alternatively, compounds of formula (II) may be prepared according to the following reaction Scheme II:

In this Scheme, a compound of formula (VIII) is treated with a secondary amine $NHR_1R_2$ (in which $R_1$ and $R_2$ are as defined earlier) in the presence of a reducing hydride, such as $NaCNBH_3$, to form a compound of formula (VII). The latter is then reduced catalytically using hydrogen/$PtO_2$ to form a diamine of formula (II).

The compounds of formulae (VII), (VI), (V) and (IV) are generically or specifically disclosed in the above mentioned European Application No. 361791.

The compounds of formula (VIII) are known compounds or can be prepared from known compounds by known methods, such as those disclosed in Chem. Berichte 34,4253; J. Org. Chem. 26(1961), 4415; J. Am. Chem. Soc. 78(1956), 5842.

The compound of formula (III) and its active derivatives, as hereinbefore defined, are also known compounds, and are disclosed in EP-A-333315.

The activity of the compounds of formula (I) in standard tests indicates that they are of potential therapeutic utility in the treatment of pain and of cerebral ischaemia.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain, or in the manufacture of a medicament for the treatment of cerebral ischaemia.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents or agents for the treatment of cerebral ischaemia.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain or for the treatment of cerebral ischaemia.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinyl-pyrrolidone, sodium starch glycollate or microcrystalline cellulose; or pharmaceutically acceptable setting agents such as sodium lauryl sulphate.

Solid compositions may be obtained by conventional methods of blending, filling tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects are observed with compounds of the invention.

The present invention also provides a method for the treatment and/or prophylaxis of pain and/or cerebral ischaemia in mammals, particularly humans, which comprises administering to the mammal in need of such treatment and/or prophylaxis an effective amount of a compound of formula (I) or a pharmaceutically acceptable salt or solvate thereof. Compounds of this invention and their preparation are illustrated in the following Examples and compounds of the Examples are summarised in Table I. The pharmacological data are summarised in Table II.

EXAMPLE 1

(2S)-1-[1-oxo-3,4-dihydro-(2H)-napht-6-yl]acetyl-2-dimethyl-aminomethyl piperidine hydrochloride.

2.0 g (14.08 mmoles) of (2S)-2-dimethylaminomethyl piperidine were dissolved in 50 ml of dry chloroform. 1.94 g (14.06 mmoles) of anhydrous potassium carbonate were added and the mixture cooled at $-10°$ C. 3.6 g (16.17 mmoles) of crude 1-oxo-3,4-dihydro-(2H)-napht-6-yl acetyl chloride [obtained from 3.3 g of 1-oxo-3,4-dihydro-(2H)-napht-6-yl acetic acid as described in EP-0333315] dissolved in 20 ml of dry chloroform, were added dropwise and the reaction mixture allowed to reach room temperature. After three hours 30 ml of water were added and the resulting biphasic solution stirred for additional 30'. The separated organic layer was washed with water, dried over $Na_2SO_4$ and concentrated in vacuo. The residue was purified by flash column chromatography on 230–400 mesh silica gel, eluting with a mixture of $CH_2Cl_2$/MeOH/28%

NH4OH, 94:4.5:0.4 respectively, to afford 2.6 g of the free base, which was dissolved in 50 ml of acetone and the solution brought to acidic pH with HCl/Et2O. The precipitate was filtered, washed and dried, to yield 2.3 g of the title compound.

$C_{20}H_{28}N_2O_2 \cdot HCl$   M.P.=208°–210° C. M.W.=364.905 $[\alpha]_D^{20}$=−64.0 (C=1, MeOH) Elemental analysis: Calcd. C,65.83; H,8.01; N,7.68; Cl,9.72; Found C,65.32; H,7.98; N,7.53; Cl,9.54. I.R. (KBr): 3450; 2950; 1680; 1625; 1605 cm$^{-1}$ N.M.R. (CDCl3): δ11.80 (s broad, 1H); 8.00 (d, 1H); 7.05–7.40 80 MHz (m, 2H); 5.10–5.45 (m, 1H); 3.10–4.30 (m, 5H); 2.40–3.10 (m, 11H); 1.90–2.30 (m, 2H); 1.10–1.85 (m, 6H).

EXAMPLE 2

(2S)-1-[1-oxo-3,4-dihydro-(2H)-napht-6-yl]acetyl-2-(N-methyl-N-ethyl)aminomethyl piperidine hydrochloride.

Prepared as described in Ex. No. 1, from 1.1 g (7.04 mmoles) of (2S)-2-(N-methyl-N-ethyl)aminomethyl piperidine, 1.0 g (7.24 mmoles) of anhydrous potassium carbonate and 1.8 g (8.09 mmoles) of crude 1-oxo-3,4-dihydro-(2H)-napht-6-yl acetyl chloride in 40 ml of dry chloroform. The crude product was purified by 230–400 mesh silica gel flash column chromatography, eluting with a mixture of CH2Cl2/MeOH/28% NH4OH, 94:6:0.5 respectively, to afford 1.2 g of the free base, which was dissolved in 30 ml of acetone and the solution brought to acidic pH with HCl/Et2O. The precipitate was filtered, washed and dried, to yield 0.9 g of the title compound.

$C_{21}H_{30}N_2O_2 \cdot HCl$   M.P.=163°–165° C. M.W.=378.931 $[\alpha]_D^{20}$=−62.5 (C=1, MeOH) Elemental analysis: Calcd. C,66.56; H,8.25; N,7.39; Cl,9.36; Found C,66.34; H,8.29; N,7.28; Cl,9.23. I.R. (KBr): 3440; 2950; 1680; 1630; 1610 cm$^{-1}$ N.M.R. (CDCl3): δ11.75 (s broad, 1H); 8.00 (d, 1H); 7.10–7.30 80 MHz (m, 2H); 5.10–5.40 (m, 1H); 2.50–4.25 (m, 15H); 1.90–2.20 (m, 2H); 1.20–1.80 (m, 9H).

EXAMPLE 3

(2S)-1-[1-oxo-3,4-dihydro-(2H)-napht-6-yl]acetyl-2-diethylaminomethyl piperidine hydrochloride.

Prepared as described in Ex. No. 1, from 1.0 g (5.87 mmoles) of (2S)-2-diethylaminomethyl piperidine, 0.83 g (6.01 mmoles) of anhydrous potassium carbonate and 1.5 g (6.75 mmoles) of crude 1-oxo-3,4-dihydro-(2H)-napht-6-yl acetyl chloride in 35 ml of dry chloroform. The crude product was purified by 230–400 mesh silica gel flash column chromatography, eluting with a mixture of CH2Cl2/MeOH/28% NH4OH, 94:5:0.5 respectively, to afford 800 mg of the free base, which was dissolved in 30 ml of ethyl acetate, containing 5% of acetone, and the solution was brought to acidic pH with HCl/Et2O. The precipitate was filtered, washed and dried, to yield 600 mg of the title compound.

$C_{22}H_{32}N_2O_2 \cdot HCl$   M.P.=136°–137° C. M.W.=392.957 $[\alpha]_D^{20}$=61.6 (C=1, MeOH) Elemental analysis: Calcd. C,67.24; H,8.47; N,7.13; Cl,9.02; Found C,66.65; H,8.30; N,7.00; Cl,8.98. I.R. (KBr): 3440; 2955; 1685; 1620; 1610 cm$^{-1}$

EXAMPLE 4

(±)-1-[1-oxo-3,4-dihydro-(2H)-napht-6-yl]acetyl-2-dimethylaminomethyl-3,3-dimethyl piperidine hydrochloride.

Prepared as described in Ex. No. 1, from 1.53 g (9.0 mmoles) of (±)-2-dimethylaminomethyl-3,3-dimethyl piperidine, 1.2 g (9.2 mmoles) of anhydrous potassium carbonate and 2.0 g (9.2 mmoles) of crude 1-oxo-3,4-dihydro-(2H)-napht-6-yl acetyl chloride in 40 ml of dry chloroform. The crude product was purified by 230–400 mesh silica gel flash column chromatography, eluting with a mixture of CH2Cl2/MeOH/28% NH4OH, 94:6:0.5 respectively, to afford 1.2 g of the free base, which was dissolved in 30 ml of ethyl acetate and the solution brought to acidic pH with HCl/Et2O. The precipitate was filtered, washed and dried, to yield 0.4 g of the title compound.

$C_{22}H_{32}N_2O_2 \cdot HCl$   M.P.=253°–255° C. M.W.=392.957 Elemental analysis: Calcd. C,67.23; H,8.46; N,7.13; Cl,9.02; Found C,65.95; H,8.19; N,7.00; Cl,8.98. I.R. (KBr): 3440; 2950; 1685; 1620; 1605 cm$^{-1}$ N.M.R. (CDCl3): δ12.1–11.1 (s broad, 1H); 8.1–7.9 (m, 1H); 80 MHz 7.4–7.1 (m, 2H); 4.9–4.6 (m, 1H); 4.2–3.1 (m, 5H); 3.1–2.8 (m, 9H); 2.8–1.9 (m, 4H); 1.6–1.1 (m, 4H); 1.1–0.7 (m, 6H).

EXAMPLE 5

(±)-1-[1-oxo-3,4-dihydro-(2H)-napht-6-yl]acetyl-2-dimethylaminomethyl-4,4-dimethyl piperidine hydrochloride.

Prepared as described in Ex. No. 1, from 0.7 g (4.11 mmoles) of (±)-2-dimethylaminomethyl-4,4-dimethyl piperidine, 0.57 g (4.2 mmoles) of anhydrous potassium carbonate and 1.0 g (4.2 mmoles) of crude 1-oxo-3,4-dihydro-(2H)-napht-6-yl acetyl chloride in 30 ml of dry chloroform. The crude product was purified by 230–400 mesh silica gel flash column chromatography, eluting with a mixture of CH2Cl2/MeOH/28% NH4OH, 94:5:0.5 respectively, to afford 0.9 g of the free base, which was dissolved in 20 ml of ethyl acetate and the solution brought to acidic pH with HCl/Et2O. The precipitate was filtered, washed and dried, to yield 0.3 g of the title compound.

$C_{22}H_{32}N_2O_2 \cdot HCl$   M.P.=214°–216° C. M.W.=392.957 Elemental analysis: Calcd. C,67.23; H,8.46; N,7.13; Cl,9.02; Found C,64.00; H,8.14; N,6.68; Cl,8.65. I.R. (KBr): 3440; 2955; 1685; 1625; 1605 cm$^{-1}$ N.M.R. (CDCl3): δ12.1–11.5 (s broad, 1H); 8.0–7.8 (m, 1H); 80 MHz 7.3–7.0 (m, 2H); 5.2–4.8 (m, 1H); 4.2–3.2 (m, 5H); 3.0–2.7 (m, 9H); 2.7–1.8 (m, 4H); 1.6–1.1 (m, 4H); 0.9 (ds, 6H).

EXAMPLE 6

(±)-1-[1-oxo-3,4-dihydro-(2H)-napht-6-yl]acetyl-2-dimethylaminomethyl-5,5-dimethyl piperidine hydrochloride.

Prepared as described in Ex. No. 1, from 1.0 g (5.9 mmoles) of (±)-2-dimethylaminomethyl-5,5-dimethyl piperidine, 1.0 g (6.5 mmoles) of anhydrous potassium carbonate and 1.6 g (6.5 mmoles) of crude 1-oxo-3,4-dihydro-(2H)-napht-6-yl acetyl chloride in 40 ml of dry chloroform. The crude product was purified by 230–400 mesh silica gel flash column chromatography, eluting with a mixture of CH2Cl2/MeOH/28% NH4OH, 94:5:0.5 respectively, to afford 1.1 g of the free base, which was dissolved in 30 ml of ethyl acetate and the solution brought to acidic pH with HCl/Et2O. The precipitate was filtered, washed and dried, to yield 0.4 g of the title compound.

$C_{22}H_{32}N_2O_2 \cdot HCl$   M.P.=188°–190° C. M.W.=392.957 Elemental analysis: Calcd. C,67.23; H,8.46; N,7.13; Cl,9.02; Found C,66.39; H,8.43; N,7.00; Cl,8.81. I.R. (KBr): 3440; 2950; 1690; 1620; 1605 cm$^{-1}$ N.M.R. (CDCl3): δ12.0–11.2 (s broad, 1H); 8.1–7.9 (m, 1H); 80 MHz 7.3–7.1 (m, 2H); 5.4–5.0 (m, 1H); 4.4–3.1

(m, 6H); 3.1–2.8 (m, 8H); 2.8–2.5 (m, 2H); 2.4–1.8 (m, 2H); 1.7–1.2 (m, 4H); 0.9 (ds, 6H).

EXAMPLE 7

(±)-1-[1-oxo-3,4-dihydro-(2H)-napht-6-yl]acetyl-2-(1-dimethylamino)ethyl piperidine hydrochloride Diastereoisomer A.

Prepared as described in Ex. No. 1, from 1.95 g (12.50 mmoles) of (±)-2-(1-dimethylamino)ethyl piperidine [1/1 diastereo-isomeric mixture], 1.8 g (13.0 mmoles) of anhydrous potassium carbonate and 3.3 g (14.83 mmoles) of crude 1-oxo-3,4-dihydro-(2H)-napht-6-yl acetyl chloride in 60 ml of dry chloroform. The crude mixture was purified by 230–400 mesh silica gel flash column chromatography, eluting with a mixture of AcOEt/28% NH4OH, 50:0.3 respectively, to afford 0.8 g of the less polar free base, which was dissolved in 25 ml of acetone and the solution brought to acidic pH with HCl/Et2O. The precipitate was filtered, washed and dried, to yield 600 mg of the title compound.

$C_{21}H_{30}N_2O_2 \cdot HCl$ M.P.=199°–200 ° C. M.W.=378.931 Elemental analysis: Calcd. C,66.56; H,8.25; N,7.39; Cl,9.36; Found C,65.35; H,8.23 N,7 20; Cl,9.41. I.R. (KBr): 3450; 2940; 1680; 1625; 1605; 1435 cm$^{-1}$

EXAMPLE 8

(±)-1-[1-oxo-3,4-dihydro-(2H)-napht-6-yl]acetyl-2-(1-dimethylamino)ethyl piperidine hydrochloride Diastereoisomer B.

Continuing the elution of the chromatographic column of the previous example with a mixture of AcOEt/MeOH/28% NH4OH, 50:1.5:0.4 respectively, 1.1 g of a second free base were obtained. This product was dissolved in 30 ml of acetone and brought to acidic pH with HCl/Et2O. The precipitate was filtered, washed and dried, to yield 800 mg of the title compound.

$C_{21}H_{30}N_2O_2 \cdot HCl$ M.P.=215°–216° C. M.W.=378.931 Elemental analysis: Calcd. C,66.56; H,8.25; N,7.39; Cl,9.36; Found C,65.68; H,8.29; N,7.25; Cl,9.83. I.R. (KBr): 3460; 2940; 1675; 1635; 1615; 1440; 1285; 1235 cm$^{-1}$

EXAMPLE 9

(2S)-1-[1-oxo-3,4-dihydro-(2H)-napht-6-yl]acetyl-2-(N-methyl-N-propyl)aminomethyl piperidine hydrochloride.

Prepared as described in Ex. No. 1, from 1.14 g (6.69 mmoles) of (2S)-2-(N-methyl-N-propyl)aminomethyl piperidine, 1.00 g (7.24 mmoles) of anhydrous potassium carbonate and 1.53 g (6.87 mmoles) of crude 1-oxo-3,4-dihydro-(2H)-napht-6-yl acetyl chloride in 45 ml of dry chloroform. The crude product was purified by 230–400 mesh silica gel flash column chromatography, eluting with a mixture of Et2O/MeOH/28% NH4OH, 100:1.5:0.6 respectively, to afford 1.0 g of the free base, which was dissolved in 30 ml of ethyl acetate and the solution brought to acidic pH with HCl/Et2O. The precipitate was filtered, washed and dried, to yield 0.8 g of the title compound.

$C_{22}H_{32}N_2O_2 \cdot HCl$ M.P.=155°–158° C. M.W.=392.957 $[\alpha]_D^{20}=-56.6$ (C=1, MeOH) Elemental analysis: Calcd. C,67.24; H,8.46; N,7.13; Cl,9.02; Found C,66.69; H,8.41; N,7.02; Cl,9.10. I.R. (KBr): 3440; 2940; 1685: 1635; 1605 cm$^{-1}$

EXAMPLE 10

(2S)-1-[1-oxo-3,4-dihydro-(2H)-napht-6-yl]acetyl-2-(N-methyl-N-isopropyl)aminomethyl piperidine hydrochloride emihydrate.

Prepared as described in Ex. No. 1, from 1.1 g (6.46 mmoles) of 2S)-2-(N-methyl-N-isopropyl)aminomethyl piperidine, 1.0 g (7.24 mmoles) of anhydrous potassium carbonate and 1.9 g (8.54 mmoles) of crude 1-oxo-3,4-dihydro-(2H)-napht-6-yl acetyl chloride in 40 ml of dry chloroform. The crude product was purified by 230–400 mesh silica gel flash column chromatography, eluting with a mixture of CH2Cl2/MeOH/28% NH4OH, 94:6:0.5 respectively, to afford 1.4 g of the free base, which was dissolved in 30 ml of ethyl acetate, containing 20% of diethyl ether, and the solution brought to acidic pH with HCl/Et2O. The precipitate was filtered, washed and dried, to yield 1.2 g of the title compound.

$C_{22}H_{32}N_2O_2 \cdot \frac{1}{2} H_2O$ M.P.=159°–160° C. M.W.=401.965 $[\alpha]_D^{20}=-62.1$ (C=1, MeOH) Elemental analysis: Calcd C,65 73; H,8.53; N,6.97; Cl,8.82 Found C,65.70; H,8.41; N,6.87; Cl,9.13. I.R. (KBr): 3550; 3480; 2940; 1680; 1635; 1605 cm$^{-1}$ N.M.R. (CDCl3): δ11.30 (s broad, 1H); 8.00 (d, 1H); 7.10–7.30 (80 MHz) (m, 2H): 5.10–5.40 (m, 1H); 3.20–4.50 (m, 6H); 2.40–3.10 (m, 8H); 1.10–2.30 (m, 14H).

EXAMPLE 11

(2S)-1-[1-oxo-3,4-dihydro-(2H)-napht-6-yl]acetyl-2-(N-allyl-N-methyl)aminomethyl piperidine hydrochloride.

Prepared as described in Ex. No. 1, from 1.15 g (6.80 mmoles) of (2S)-2-(N-allyl-N-methyl)aminomethyl piperidine, 1.00 g (7.24 mmoles) of anhydrous potassium carbonate and 1.67. g (7.50 mmoles) of crude 1-oxo-3,4-dihydro-(2H)-napht-6-yl acetyl chloride in 35 ml of dry chloroform. The crude product was purified by 230–400 mesh silica gel flash column chromatography, eluting with a mixture of EtOAc/n-hexane 6:4, containing 0.2% of 28% NH4OH, to afford 0.5 g of the free base, which was dissolved in 15 ml of ethyl acetate and the solution brought to acidic pH with HCl/Et2O. The precipitate was filtered, washed and dried, to yield 0.35 g of the title compound.

$C_{22}H_{30}N_2O_2 \cdot HCl$ M.P.=183°–184° C. M.W.=390.941 $[\alpha]_D^{20}=-60.3$ (C=1, MeOH) Elemental analysis: Calcd. C,67.59; H,7.74; N,7.16; Cl,9.07; Found C,67.31; H,7.83; N,7.06; Cl,9.02. I.R. (KBr): 3430; 2940; 1685; 1625; 1605 cm$^{-1}$

EXAMPLE 12

(2S)-1-[1-oxo-3,4-dihydro-(2H)-napht-6-yl]acetyl-2-(N-cyclopropyl-N-methyl)aminomethyl piperidine hydrochloride.

Prepared as described in Ex. No. 1, from 1.4 g (8.32 mmoles) of (2S)-2-(N-cyclopropyl-N-methyl)aminomethyl piperidine, 1.2 g (8.69 mmoles) of anhydrous potassium carbonate and 2.0 g (8.98 mmoles) of crude 1-oxo-3,4-dihydro-(2H)-napht-6-yl acetyl chloride in 40 ml of dry methylene chloride. The crude product was purified by 230–400 mesh silica gel flash column chromatography, eluting with a mixture of EtOAc/n-hexane 6:4, containing 0.2% of 28% NH4OH, to afford 0.85 g of the free base, which was dissolved in 20 ml of ethyl acetate and the solution brought to acidic pH with HCl/Et2O. The precipitate was filtered, washed and dried, to yield 0.65 g of the title compound.

$C_{22}H_{30}N_2O_2 \cdot HCl$    M.P.=172°–174° C. M.W.=390.941 $[\alpha]_D^{20}=-55.6$ (C=1, MeOH) Elemental analysis: Calcd. C,67.59; H,7.99; N,7.17; Cl,9.07; Found C,67.65; H,7.98; N,7.98; Cl,9.04. I.R. (KBr): 3440; 2930: 1675; 1625; 1605 cm$^{-1}$

EXAMPLE 13

(2S)-1-oxo-3,4-dihydro-(2H)-napht-6-yl]acetyl-2-(N-methyl-N-tbutyl)aminomethyl piperidine hydrochloride.

Prepared as described in Ex. No. 1, from 0.41 g (2.23 mmoles) of (2S)-2-(N-methyl-N-tbutyl)aminomethyl piperidine, 0.4 g (2.90 mmoles) of anhydrous potassium carbonate and 0.6 g (2.70 mmoles) of crude 1-oxo-3,4-dihydro-(2H)-napht-6-yl acetyl chloride in 20 ml of dry chloroform. The crude product was purified by 230–400 mesh silica gel flash column chromatography, eluting with a mixture of EtOAc/n-hexane 6:4, containing 0.3% of 28% NH$_4$OH, to afford 0.35 g of the free base, which was dissolved in 15 ml of ethyl acetate and the solution brought to acidic pH with HCl/Et$_2$O. The very hygroscopic material was filtered, washed and dried, to yield 0.25 g of the title compound.

$C_{23}H_{34}N_2O_2 \cdot HCl$    M.P.=110°–114° C. M.W.=406.983 $[\alpha]_D^{20}=-19.7$ (C=1, MeOH) I.R. (KBr): 3450; 2940; 1675; 1630; 1605 cm$^{-1}$

EXAMPLE 14

(±)-1-[1-oxo-3,4-dihydro-(2H)-napht-6-yl]acetyl-2-dimethylaminomethyl4,4-dimethyipiperidine L(+) tartrate.

2.2 g (6.2 mmoles) of the compound of Ex. No. 5 (as free base) were dissolved in 30 ml of abs. ethanol. 0.95 g (6.4 mmoles of L(+) tartaric acid, dissolved in 30 ml of abs. ethanol, were added to the hot solution of the free base. After a gentle warming, the solution was filtered and the less soluble diastereoisomeric salt crystallized on standing. The salt was recrystallized from ethanol, up to a constant rotatory power, to give 0.7 g of the title compound.

$C_{22}H_{32}N_2O_2 \cdot L(+)$  $C_4H_6O_6$  M.P.=174°–175° C. M.W.=506.580 $[\alpha]_D^{20}=+44.5$ (C=1, MeOH)

A sample of the L(+) tartrate salt was transformed into the free base by dissolving in acq. NH$_3$ solution, extracting with diethyl ether and evaporating the solvent in vacuo. The obtained free base was dissolved in ethyl acetate and transformed into the hydrochloride salt by treatment with HCl/Et$_2$O.

The salt gave an $[\alpha]_D^{20}=+47.0$ (C=1, MeOH) The I.R. and N.M.R. spectra were identical to those obtained for the racemate.

EXAMPLE 15

(−)-1-[1-oxo-3,4-dihydro-(2H)-napht-6-yl]acetyl-2-dimethylaminomethyl-4,4-dimethylpiperidine D(−) tartrate.

The mother liquors of the first crystallization of Ex. No. 14 were evaporated in vacuo to dryness. The residue was treated with acq. NH$_3$ solution and extracted with diethyl ether to afford 1.12 g (3.14 mmoles) of the enriched free base, which was dissolved in 30 ml of abs. ethanol. 0.47 g (3.14 mmoles) of D(−) tartaric acid, dissolved in abs. ethanol, were added to the warm solution and the diastereoisomeric salt crystallized on standing. The salt was recrystallized from ethanol, up to a constant rotatory power, to give 0.5 g of the title compound.

$C_{22}H_{32}N_2O_2 \cdot D(-)$  $C_4H_6O_6$  M.P.=173°–174° C. M.W.=506.580 $[\alpha]_D^{20}=-43.5$ (C=1, MeOH)

A sample of the D(−) tartrate was transformed into the corresponding hydrochloride salt following the same procedure described in the Ex. No. 14. This salt gave an $[\alpha]_D^{20}=-46.2$ (C=1, MeOH) The I.R. and N.M.R. spectra were identical to those obtained for the racemate.

EXAMPLE 16

(2S)-1-[1-oxo-3,4-dihydro-(2H)-napht-6-yl]acetyl-2-(N-methyl-N-propargyl)aminomethyl piperidine hydrochloride Prepared as described in Ex. No. 1, from 700 mg (4.21 mmoles) of crude (2S)-2-(N-methyl-N-propargyl)aminomethyl piperidine, 600 mg (4.34 mmoles) of anhydrous potassium carbonate and 1.08 g (4.83 mmoles) of crude 1-oxo-3,4-dihydro-(2H)-napht-6-yl acetyl chloride in 30 ml of dry chloroform. The crude product was purified by 230–400 mesh silica gel flash column chromatography, eluting with a mixture of ethyl acetate/n-hexane 8:2, containing 0.5% of 28% NH$_4$OH, to afford 250 mg of the free base, which was dissolved in 15 ml of ethyl acetate containing 20% of ethyl ether and the solution brought to acidic pH with HCl/Et$_2$O. The precipitate was filtered, washed and dried, to yield 100 mg of the title compound.

$C_{22}H_{28}N_2O_2 \cdot HCl$    M.P.=169°–170° C. M.W.=388.925 I.R. (KBr): 3430; 2940; 1680; 1630; 1608 cm$^{-1}$ N.M.R. (CDCl$_3$): δ11.80 (s broad, 1H); 8.00 (d, 1H); 7.15–7.30 80 MHZ (m, 2H); 4.20–5.40 (m, 2H); 3.10–4.15 (m, 6H); 2.80–3.05 (m, 5H); 2.50–2.70 (m, 3H); 1.90–2.30 (m, 3H); 1.30–1.80 (m, 6H).

EXAMPLE 17

(2S)-1-[1-oxo-3,4-dihydro-(2H)-napht-6-yl]acetyl-2-(N-cyclobutyl-N-methyl)aminomethyl piperidine hydrochloride Prepared as described in Ex. No. 1, from 1.7 g (9.32 mmoles of (2S)-2-(N-cyclobutyl-N-methyl)aminomethyl piperidine, 1.5 g (10.86 mmoles) of anhydrous potassium carbonate and 2.08 g (9.35 mmoles) of crude 1-oxo-3,4-dihydro-(2H)-napht-6-yl acetyl chloride in 50 ml of dry chloroform. The crude product was purified by 230–400 mesh silica gel flash column chromatography, eluting with ethyl acetate containing 0.6% of 28% NH$_4$OH, to afford 1.7 g of the free base, which was rechromatographed on silica gel, eluting with a mixture of CH$_2$Cl$_2$/MeOH/28% NH$_4$OH, 94:15:0.3 respectively, to afford 1.4 g of the pure free base. The compound was dissolved in 30 ml of ethyl acetate and the solution brought to acidic pH with HCl/Et$_2$O. The precipitate was filtered, washed and dried, to yield 1.3 g of the title compound.

$C_{23}H_{32}N_2O_2 \cdot HCl$    M.P.=184°–186° C. M.W.=404.967 $[\alpha]_D^{20}=-58.8$ (C=1, MeOH) Elemental analysis: Calcd.: C,68.21; H,8.21; N,6.92; Cl,8.76; Found: C,68.46; H,8.18; N,6.59; Cl,8.30. I.R. (KBr): 3440; 2940; 1685; 1625; 1605 cm$^{-1}$

EXAMPLE 18

(2S)-1-[1-oxo-3,4-dihydro-(2H)-napht-6-yl]acetyl-2-(N-cyclopentyl-N-methyl)aminomethyl piperidine hydrochloride .¼ H$_2$O Prepared as described in Ex. No. 1, from 1.70 g (8.66 mmoles) of (2S)-2-(N-cyclopentyl-N-methyl)aminomethyl piperidine, 1.37 g (9.92 mmoles) of anhydrous potassium carbonate and 2.19 g (9.80 mmoles) of crude 1-oxo-3,4-dihydro-(2H)-napht-6-yl acetyl chloride in 50 ml of dry chloroform. The crude product was purified by 230-400 mesh silica gel flash column chromatography, eluting with ethyl acetate containing 0.6% of 28% NH$_4$OH, to afford 1.90 g of the pure free base, which was dissolved in 40 ml of ethyl acetate and the solution brought to acidic pH with HCl/Et$_2$O. The precipitate was filtered, washed and dried, to yield 1.55 g of the title compound.

C$_{24}$H$_{34}$N$_2$O$_2$·¼ H$_2$O   M.P.=126°–129° C.
M.W.=423.497   $[\alpha]_D^{20}$=−62.1 (C=1, MeOH) Elemental analysis: Calcd.: C,68.06; H,8.45; N,6.61; Cl,8.37; Found: C,68.11; H,8.42; N,6.54; Cl,8.3 I.R. (KBr): 3450; 2940; 1680; 1630; 1605 cm$^{-1}$

EXAMPLE 19

(2S)-1-[1-oxo-3,4-dihydro-(2H)-napht-6-yl]acetyl-2-(N-cyclopropylmethyl-N-methyl)aminomethyl piperidine hydrochloride Prepared as described in Ex. No. 1, from 1.35 g (7.40 mmoles) of 2S)-2-(N-cyclopropylmethyl-N-methyl-)aminomethyl piperidine 1.22 g (8.84 mmoles) of anhydrous potassium carbonate and 1.97 g (8.81 mmoles) of crude 1-oxo-3,4-dihydro-(2H)-napht-6-yl acetyl chloride in 40 ml of dry chloroform. The crude product was purified by 230-400 mesh silica gel flash column chromatography, eluting with a mixture of CH$_2$Cl$_2$/MeOH/28% NH$_4$OH, 94:2.5:0.4 respectively, to afford 1.4 g of the title compound.

C$_{23}$H$_{32}$N$_2$O$_2$·HCl   M.P.=148°–150° C.
M.W.=404.967 $[\alpha]_D^{20}$=−54.8 (C=1, MeOH) I.R. (KBr): 3440; 2940; 1685; 1625; 1605; 1425 cm$^{-1}$ N.M.R. (CDCl$_3$): δ11.80 (s broad, 1H); 8.00 (d, 1H); 7.10–7.30 80 MHz (m, 2H); 5.10–5.45 (m, 1H); 2.80–4.25 (m, 13H); 2.60 (t, 2H); 1.90–2.30 (m, 2H); 1.05–1.85 (m, 7H); 0.60–0.90 (m, 2H); 0.30–0.55 (m, 2H).

TABLE I

| Example N° | R1 | R2 | R3 | R4 | R5 | MOLECULAR FORMULA | MELTING POINT (°C.) | * | $[\alpha]_D^{20}$ (C = 1, MeOH) |
|---|---|---|---|---|---|---|---|---|---|
| 1 | CH$_3$ | CH$_3$ | H | H | H | C$_{20}$H$_{28}$N$_2$O$_2$·HCl | 208–210 | S | −64.0 |
| 2 | CH$_3$ | CH$_2$CH$_3$ | H | H | H | C$_{21}$H$_{30}$N$_2$O$_2$·HCl | 163–165 | S | −62.5 |
| 3 | CH$_2$CH$_3$ | CH$_2$CH$_3$ | H | H | H | C$_{22}$H$_{32}$N$_2$O$_2$·HCl | 136–137 | S | −61.6 |
| 4 | CH$_3$ | CH$_3$ | 3-CH$_3$ | 3-CH$_3$ | H | C$_{22}$H$_{32}$N$_2$O$_2$·HCl | 253–255 | R, S | — |
| 5 | CH$_3$ | CH$_3$ | 4-CH$_3$ | 4-CH$_3$ | H | C$_{22}$H$_{32}$N$_2$O$_2$·HCl | 214–216 | R, S | — |
| 6 | CH$_3$ | CH$_3$ | 5-CH$_3$ | 5-CH$_5$ | H | C$_{22}$H$_{32}$N$_2$O$_2$·HCl | 188–190 | R, S | — |
| 7 DIAST. A | CH$_3$ | CH$_3$ | H | H | CH$_3$ | C$_{21}$H$_{30}$N$_2$O$_2$·HCl | 199–200 | R, S | — |
| 8 DIAST. B | CH$_3$ | CH$_3$ | H | H | CH$_3$ | C$_{21}$H$_{30}$N$_2$O$_2$·HCl | 215–216 | R, S | — |
| 9 | CH$_3$ | CH$_2$CH$_2$CH$_3$ | H | H | H | C$_{22}$H$_{32}$N$_2$O$_2$·HCl | 155–158 | S | −56.6 |
| 10 | CH$_3$ | CH(CH$_3$)$_2$ | H | H | H | C$_{22}$H$_{32}$N$_2$O$_2$·HCl·½H$_2$O | 159–160 | S | −62.1 |
| 11 | CH$_3$ | CH$_2$CH=CH$_2$ | H | H | H | C$_{22}$H$_{30}$N$_2$O$_2$·HCl | 183–184 | S | −60.3 |
| 12 | CH$_3$ | cyclopropyl | H | H | H | C$_{22}$H$_{30}$N$_2$O$_2$·HCl | 172–174 | S | −55.6 |
| 13 | CH$_3$ | C(CH$_3$)$_3$ | H | H | H | C$_{23}$H$_{34}$N$_2$O$_2$·HCl | 110–114 | S | −19.7 |
| 14 | CH$_3$ | CH$_3$ | CH$_3$ | CH$_3$ | H | C$_{22}$H$_{32}$N$_2$O$_2$·L(+) C$_4$H$_6$O$_6$ | 174–175 | R | +44.5 |
| 15 | CH$_3$ | CH$_3$ | CH$_3$ | CH$_3$ | H | C$_{22}$H$_{32}$N$_2$O$_2$·D(−) C$_4$H$_6$O$_6$ | 173–174 | S | −43.5 |
| 16 | CH$_3$ | CH$_3$C≡CH | H | H | H | C$_{22}$H$_{28}$N$_2$O$_2$·HCl | 169–170 | S | — |
| 17 | CH$_3$ | cyclobutyl | H | H | H | C$_{23}$H$_{32}$N$_2$O$_2$·HCl | 184–186 | S | −58.8 |
| 18 | CH$_3$ | cyclopentyl | H | H | H | C$_{24}$H$_{34}$N$_2$O$_2$·HCl·¼H$_2$O | 126–129 | S | −62.1 |

TABLE I-continued

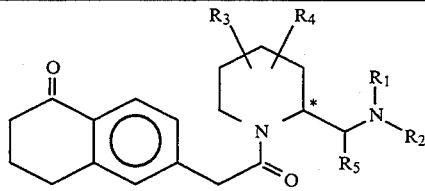

| Example N° | R1 | R2 | R3 | R4 | R5 | MOLECULAR FORMULA | MELTING POINT (°C.) | * | $[\alpha]D^{20}$ (C = 1, MeOH) |
|---|---|---|---|---|---|---|---|---|---|
| 19 | CH3 | CH2—◁ | H | H | H | $C_{23}H_{32}N_2O_2 \cdot HCl$ | 148–150 | S | −54.8 |

The pharmacological activity of the compounds of this invention is illustrated by the mouse writhing test, described as follows:

P-phenylquinone-induced abdominal writhing test in mice

The methodology employed is based on that described by Sigmund et al, Proc. Soc. Exptl. Biol. 95, 729/1957, modified by Milne and Twomey, Agents and Actions, 10, 31/1980.

Male Charles River mice (Swiss Strain), 25–36 g body weight, were used. Animals were allowed food and water ad libitum and were randomized into groups of 10 prior to experimentation. Test compounds were dissolved in either distilled water or distilled water plus 0.1M AMS, and administered by the subcutaneous route in a final volume of 10 ml/Kg. Control animals received 10 ml/Kg of the appropriate vehicle alone. Following a pretreatment period of 20 min., mice were injected intraperitoneally with p-phenylquinone, 2 mg/Kg at 37° C. in a final volume of 10 mg/kg. Next, the mice were placed, in groups of 3, in a compartmented perspex box maintained at room temperature and were observed for a period of 8 min. During this period the number of abdominal writhing responses per animal were recorded where writhing consists of an intermittent contraction of the abdomen associated with hind leg extension.

The degree of antinociceptive protection afforded by the test compound was determined as the mean number of writhing responses observed in the treated group (T) expressed as a percentage of the mean number of writhing responses in the control group (C) according to the following formula:

$$[1-(T/C)] \times 100\% = \% \text{ graded protection}$$

RECEPTOR AFFINITY STUDY

Tissue Preparation

Radio receptor binding to kappa site is performed on fresh guinea pig brain homogenates prepared according to Kosterlitz (1981).

Whole brain without cerebellum is homogenized in 50 mM Tris-buffer (pH 7.4 at 0° C.) and centrifuged at 49,000×g for 10 min.

The pellet is then resuspended in the same buffer, incubated at 37° C. for 45 min and centrifuged again.

1.9 ml of the final homogenate (1:100 in Tris pH 7.4, 0° C.) is used for the binding assay.

Binding to kappa sites

The binding to the kappa sites is performed using a tritiated kappa selective compound. Final homogenate with solutions of the cold ligand and of the labelled ligand is incubated for 40 min at 25° C., filtered through Whatman GF/C glass filter discs and washed. The radioactivity bound to the filters is counted by liquid scintillation spectrophotometry.

The non-specific binding is determined in the presence of 500 nM of the benzomorphan non-selective compound Mr 2266.

Binding to mu sites (Magnan J., 1982)

$^3$H[D-Ala$^2$, MePhe$^4$, Gly-ol$^5$] Enkephalin ($^3$H-DAGO), an enkephalin analogue that binds selectively to mu receptor, is added to the biological substrate and incubated at 25° C. for 40 min, filtered through Whatman GF-C and washed with ice-cold Tris-buffer.

The filters are then dried, solubilized in Filtercount and the radioactivity monitored. Non-specific binding is determined in the presence of $10^{-6}$M naloxone.

Binding to delta sites (Magnan J., 1982)

For binding experiments, $^3$H-DADLE, which binds to mu and delta sites, is used in the presence of 30 nM of unlabelled DAGO to prevent mu binding. A concentration of radioligand near KD is used in the binding assays evaluating compounds of the invention. Non-specific binding is determined by addition of Mr 2266 2.5 μM.

The tubes are incubated for 40 min at 25° C. and bound ligand is separated from free by filtration through Whatman GF/C filters. The level of bound radioactivity of the filters is measured by liquid scintillation after solubilization in Filtercount.

The equilibrium dissociation constant (FD) and the maximum binding capacity (Bmax) are determined from the analysis of saturation curves, while the inhibition constant (Ki) is determined from the analysis of competition experiments (Hill 1910; Scatchard 1949; Cheng and Prusoff 1973; Gillan et al 1980).

Published references are summarized as follows:

Hill, A. V. (1910): J. Physiol. 40, IV–VIII

Scatchard G. (1949): Ann. N.Y. Acad. Sci. 51, 660–674

Cheng and Prusoff W. H. (1973): Biochem. Pharmac. 22, 3099–3102

Gillan M. C. G., Kosterlitz H. W. and Paterson S. Y. (1980): Br. J. Pharmac. 70, 481–490

Kosterlitz H. W., Paterson S. Y. and Robson L. E. (1981): Br. J. Pharmac. 73, 939–949

Magnan J., Paterson S. Y., Tavani A. and Kosterlitz H. W. (1982): Arch. Pharmacol. 319, 197–205.

TABLE 11

| | Pharmacological data | |
|---|---|---|
| Example N° | ANALGESIA MOUSE WRITHING (GRADED) ED50 mg/kg s.c. | KAPPA BRAIN RECEPTOR BINDING Ki nM |
| 1 | 0.154 | 47.0 |
| 2 | 0.061 | 10.3 |
| 3 | 0.427 | 80.3 |
| 5 | 0.377 | 65.0 |
| 6 | 0.641 | 88.7 |
| 9 | 0.221 | 10-50 |
| 10 | 0.078 | 2.87 |
| 11 | 0.130 | ca 50 |
| 12 | 0.141 | 50 |
| 15 | 0.115 | 22.9 |
| 16 | 0.056 | — |
| 17 | 0.127 | — |
| 18 | 0.210 | — |

Mu and delta binding affinities for the above Examples were found to be >1000 nM.

We claim:

1. A compound, or a solvate or salt thereof, of formula (I):

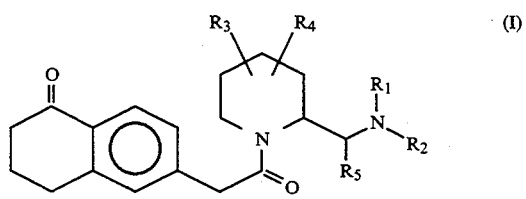

in which:
R$_1$ and R$_2$ are each linear or branched C$_{1-4}$alkyl, C$_{3-6}$cycloalkyl, C$_{4-6}$cycloalkylalkyl, C$_{3-4}$alkenyl, C$_{3-6}$cycloalkenyl or C$_{3-4}$alkynyl, R$_3$ and R$_4$ are identical, and each is hydrogen or C$_{1-4}$ alkyl; and R$_5$ is hydrogen or C$_{1-3}$alkyl.

2. A compound according to claim 1, in which R$_3$ and R$_4$ are both C$_{1-4}$ alkyl and are bonded to the same carbon atom of the piperidine ring.

3. A compound according to claim 1 in which each of R$_1$ and R$_2$ is methyl, ethyl, propyl, isopropyl, tert-butyl, cyclopropyl, cyclobutyl, cyclopentyl, cyclopropylmethyl, allyl or propynyl.

4. A compound according to claim 1 in which R$_3$ and R$_4$ are together 3,3 gem-dimethyl, 4,4 gem-dimethyl or 5,5 gem-dimethyl.

5. A compound according to claim 1 in which R$_5$ is hydrogen or methyl.

6. A compound according to claim 1 which is:
(2S)-1-[1-oxo-3,4-dihydro-(2H)-napht-6-yl]acetyl-2-dimethyl-aminomethyl piperidine;
(2S)-1-[1-oxo-3,4-dihydro-(2H)-napht-6-yl]acetyl-2-(N-methyl-N-ethyl)aminomethyl piperidine;
(2S)-1-[1-oxo-3,4-dihydro-(2H)-napht-6-yl]acetyl-2-diethylamino-methyl piperidine;
(±)-1-[1-oxo-3,4-dihydro-(2H)-napht-6-yl]acetyl-2-dimethylamino-methyl-3,3-dimethyl piperidine;
(±)-1-[1-oxo-3,4-dihydro-(2H)-napht-6-yl]acetyl-2-dimethylamino-methyl-4,4-dimethyl piperidine;
(±)-1-[1-oxo-3,4-dihydro-(2H)-napht-6-yl]acetyl-2-dimethylamino-methyl-5,5-dimethyl piperidine;
(±)-1-[1-oxo-3,4-dihydro-(2H)-napht-6-yl]acetyl-2-(1-dimethylamino)ethyl piperidine Diastereoisomer A;
(±)-1-[1-oxo-3,4-dihydro-(2H)-napht-6-yl]acetyl-2-(1-dimethylamino)ethyl piperidine Diastereoisomer B;
(2S)-1-[1-oxo-3,4-dihydro-(2H)-napht-6-yl]acetyl-2-(N-methyl-N-propyl)aminomethyl piperidine;
(2S)-1-[1-oxo-3,4-dihydro-(2H)-napht-6-yl]acetyl-2-(N-methyl-N-isopropyl)aminomethyl piperidine;
(2S)-1-[1-oxo-3,4-dihydro-(2H)-napht-6-yl]acetyl-2-(N-allyl-N-methyl)aminomethyl piperidine;
(2S)-1-[1-oxo-3,4-dihydro-(2H)-napht-6-yl]acetyl-2-(N-cyclopropyl-N-methyl)aminomethyl piperidine;
(2S)-1-[1-oxo-3,4-dihydro-(2H)-napht-6-yl]acetyl-2-(N-methyl-N-butyl)aminomethyl piperidine;
(+)-1-[1-oxo-3,4-dihydro-(2H)-napht-6-yl]acetyl-2-dimethylaminomethyl-4,4-dimethylpiperidine L(+)tartrate;
(−)-1-[1-oxo-3,4-dihydro-(2H)-napht-6-yl]acetyl-2-dimethylaminomethyl-4,4-dimethylpiperidine D(−)tartrate;
(2S)-1-[1-oxo-3,4-dihydro-(2H)-napht-6-yl]acetyl-2-(N-methyl-N-propargyl)aminomethyl piperidine;
(2S)-1-[1-oxo-3,4-dihydro-(2H)-napht-6-yl]acetyl-2-(N-cyclobutyl-N-methyl)aminomethyl piperidine;
(2S)-1-[1-oxo-3,4-dihydro-(2H)-napht-6-yl]acetyl-2-(N-cyclopentyl-N-methyl)aminomethyl piperidine; or
(2S)-1-[1-oxo-3,4-dihydro-(2H)-napht-6-yl]acetyl-2-(N-cyclo-propylmethyl-N-methyl)aminomethyl piperidine.

7. A pharmaceutical composition comprising a compound according to claim 1 and a pharmaceutically acceptable carrier.

8. A method for the treatment of pain and/or cerebral ischaemia in mammals, which comprises administering to the mammal in need of said treatment an effective amount of a compound according to claim 1.

* * * * *